(12) United States Patent
Hayashi et al.

(10) Patent No.: US 8,048,399 B2
(45) Date of Patent: Nov. 1, 2011

(54) ULTRAFINE PARTICLE OF RUTILE-TYPE TITANIUM OXIDE

(75) Inventors: Toyoharu Hayashi, Yokohama (JP);
Norio Nakayama, Ichihara (JP);
Tomonori Iijima, Ichihara (JP)

(73) Assignee: Mitsui Chemicals, Inc., Minato-Ku, Tokyo (JP)

( * ) Notice: Subject to any disclaimer, the term of this patent is extended or adjusted under 35 U.S.C. 154(b) by 0 days.

(21) Appl. No.: 12/591,876

(22) Filed: Dec. 3, 2009

(65) Prior Publication Data

US 2010/0080752 A1 Apr. 1, 2010

Related U.S. Application Data (62) Division of application No. 11/659,540, filed as application No. PCT/JP2005/014280 on Aug. 4, 2005, now abandoned.

(30) Foreign Application Priority Data

Aug. 26, 2004 (JP) ................................. 2004-246745

(51) Int. Cl.
*C01G 23/047* (2006.01)
*C01G 23/053* (2006.01)
*B01J 21/06* (2006.01)

(52) U.S. Cl. .......................... 423/610; 423/611; 502/350

(58) Field of Classification Search .................. 423/610, 423/611; 502/350
See application file for complete search history.

(56) References Cited

U.S. PATENT DOCUMENTS

| 2,113,946 | A | 4/1938 | Plechner et al. |
| 4,923,682 | A | 5/1990 | Roberts et al. |
| 5,149,519 | A | 9/1992 | Chopin et al. |
| 5,973,175 | A | 10/1999 | Bruno |
| 6,328,947 | B1 | 12/2001 | Monden et al. |
| 6,420,437 | B1 * | 7/2002 | Mori et al. ..................... 516/90 |
| 6,440,383 | B1 | 8/2002 | Duyvesteyn et al. |
| 6,610,135 | B1 | 8/2003 | Ohmori et al. |
| 7,138,357 | B2 | 11/2006 | Karvinen et al. |

FOREIGN PATENT DOCUMENTS

| JP | 07000819 | 1/1995 |
| JP | 2001-031421 | 2/2001 |
| TW | 460406 | 1/2001 |
| WO | WO 03/082743 | 10/2003 |

OTHER PUBLICATIONS

S.R. Dhage, Renu Pasricha, V. Ravi, "Synthesis of Itrafine TiO2 by citrate gel method," Materials Research Bulletin 38 (2003), pp. 1623-1628.*

(Continued)

*Primary Examiner* — Stanley Silverman
*Assistant Examiner* — Diana J Liao
(74) *Attorney, Agent, or Firm* — Buchanan Ingersoll & Rooney PC (57) ABSTRACT

It is provided ultrafine particles of a rutile titanium oxide obtained by maintaining the pH of an aqueous solution of a titanium compound having a Ti concentration of from 0.07 to 5 mol/L in the range of −1 to 3 in the presence of a chelating agent. Such ultrafine particles of a rutile titanium oxide are useful for photocatalysts, high refractive index materials, ultraviolet absorbing materials and the like.

8 Claims, 5 Drawing Sheets

1: Rutile-type titanium oxide air-dried in Example 1
2: Rutile-type titanium oxide calcined at 400 degree centigrade in Example 1
3: Comparative Example 2
4: Methylene blue alone without adding titanium oxide

OTHER PUBLICATIONS

S. R. Dhage, S. P. Gaikwad and V. Ravi, "Synthesis of nanocrystalline TiO2 by tartarate gel method," Bulletin of Materials Science vol. 27 No. 6 (2004), pp. 487-489.*

Benpeng Jiang, Hengbo Yin, Tingshun Jiang, Jing Yan, Zhen Fan, Changsheng Li, Jing Wu, Yuji Wada, "Size-controlled synthesis of anatase TiO2 nanoparticles by carboxylic acid group-containing organics" Materials Chemistry and Physics 92 (2005), pp. 595-599.*

Office Action issued in the corresponding Chinese Patent Application No. 200580028351.2 dated Apr. 27, 2010.

Hee-Dong Nam et al., "Preparation of Ultrafine Crystalline $TiO_2$ Powders from Aqueous $TiCl_4$ Solution by Precipitation", Japanese Journal of Applied Physics Part 1 Regular Papers Short Notes & Review Papers, Aug. 1998, pp. 4603-4608, vol. 37, No. 8, The Japan Society of Applied Physics.

Cheng, Humin, Jiming Ma, Zhenguo Zhao, and Limin Qi, "Hydrothermal Preparation of Uniform Nanosize Rutile and Anatase Particles," Chem. Mater. 7 (1995), pp. 663-671.

Extended European Search Report issued in corresponding European Application No. EP 05 76 8650 dated Sep. 3, 2010.

* cited by examiner

1: Rutile-type titanium oxide air-dried in Example 1
2: Rutile-type titanium oxide calcined at 400 degree centigrade in Example 1
3: Comparative Example 2
4: Methylene blue alone without adding titanium oxide

Fig. 4

1: Rutile-type titanium oxide calcined at 400 degree centigrade in Example 2

2: Acetoaldehyde alone without adding titanium oxide

Fig. 5

1: Rutile-type titanium oxide calcined at 400 degree centigrade in Example 3

2: Toluene alone without adding titanium oxide

ULTRAFINE PARTICLE OF RUTILE-TYPE TITANIUM OXIDE

CROSS REFERENCE TO RELATED APPLICATION

This application is a divisional of U.S. patent application Ser. No. 11/659,540, filed Feb. 6, 2007, which in turn is the United States national phase of International Application No. PCT/JP2005/014280, filed Aug. 4, 2005, published in Japanese as International Publication No. WO 2006/022130 A1 on Mar. 2, 2006, and claims priority to Japanese Application No. 2004-246745, filed Aug. 26, 2004, each hereby expressly incorporated by reference in its entirety and each assigned to the assignee hereof.

TECHNICAL FIELD

The present invention relates to ultrafine particles of a rutile-type titanium oxide which are useful for photocatalysts, high refractive index materials, ultraviolet absorbing materials and the like.

BACKGROUND ART

Titanium oxide has been known as a typical photo-oxidation catalyst, and hitherto applied to an antibacterial agent, an antifogging agent that utilizes their super hydrophilicity, or the like. There have been known three types of crystal structures for titanium oxide; anatase, rutile and brookite. Of these types, anatase is considered to have the highest photocatalytic activity. In recent years, however, it has been known that the photocatalytic activity is further enhanced by bringing a rutile-type component partially into contact with an anatase-type component and mixing them. For that reason, there has been proposed that ultrafine particles of a rutile-type titanium oxide are mixed with an anatase-type titanium oxide. It has also been expected that high activity is exhibited by using ultrafine particles of a rutile-type titanium oxide alone. However, since in the conventional vapor phase method, a rutile-type titanium oxide is treated at a high temperature, its particle diameter becomes large due to sintering. Thus, there has been a drawback such that the photocatalytic activity is consequently reduced due to the decrease in the surface area.

On the other hand, there has been reported a method for synthesizing a rutile-type titanium oxide using the low temperature wet prosess by H. D. Nam et al. (Non-patent Document 1). However, in this method, there is also the problem of decrease in the photocatalytic activity because there is formed an aggregate having a particle diameter of 200 to 400 nm in which a long-fibrous rutile-type titanium oxide is gathered. In order to overcome these drawbacks, it is also provided highly dispersive rutile ultrafine particles useful for high refractive index materials or ultraviolet absorbing materials requiring transparency.

Non-patent Document 1: Jpn. J. Appl. Phys., Vol. 37, p. 4603 (1998)

DISCLOSURE OF THE INVENTION

An object of the present invention is to provide ultrafine particles of a rutile-type titanium oxide which are used for photocatalysts, high refractive index materials, ultraviolet absorbing materials and the like.

In order to solve the above problems, the present inventors have conducted an extensive investigation, and as a result, have found that the increase in a crystal grain diameter is suppressed and the aggregation of a crystal is also suppressed in the event that a chelating agent is used in the preparation of a rutile-type titanium oxide. Thus, the present invention has been completed.

That is, the present invention relates to ultrafine particles of a rutile-type titanium oxide obtained by maintaining the pH of an aqueous solution of a titanium compound having a Ti concentration of 0.07 to 5 mol/L in the range of −1 to 3 in the presence of a chelating agent.

EFFECT OF THE INVENTION

According to the present invention, it can be provided novel ultrafine particles of a rutile-type titanium oxide and a photocatalyst containing the ultrafine particles of a rutile-type titanium oxide.

BEST MODE FOR CARRYING OUT THE INVENTION

Ultrafine particles of a rutile-type titanium oxide of the present invention are obtained by maintaining the pH of an aqueous solution of a titanium compound having a Ti content concentration of 0.07 to 5 mol/L in the range of −1 to 3 in the presence of a chelating agent.

The chelating agent to be used for the preparation of ultrafine particles of a rutile-type titanium oxide of the present invention is not particularly limited as far as it has at least two functional groups capable of coordinating to titanium cations.

Examples of the compound having at least two functional groups capable of coordinating to titanium cations include hydroxycarboxylic acids, diketones, ketocarboxylic acids, keto esters and dicarboxylic acids.

For preparing of ultrafine particles of a rutile-type titanium oxide of the present invention, one or more agents selected from hydroxycarboxylic acids, diketones, ketoesters and dicarboxylic acids may be used.

Examples of the hydroxycarboxylic acids include glycolic acid, lactic acid, citric acid, tartaric acid, salicylic acid, and salts thereof such as sodium citrate and the like. Examples of the diketones include acetylacetone, propionylacetone and salts thereof such as aluminum acetylacetonate and the like.

Examples of the keto esters include ethyl acetoacetate, ethyl malonate and the like.

Examples of the dicarboxylic acids include malonic acid, succinic acid and the like.

The amount of the chelating agent to the titanium compound to be used is selected such that a mole ratio of the chelating agent to the Ti content in the titanium compound is in the range of 0.0005 to 0.05. It is desired that the chelating agent is used within this range because it is difficult for ultrafine particles of a rutile-type titanium oxide to aggregate and form a huge aggregate within above range.

The titanium compound to be used in the present invention is not limited as far as it forms titanium oxide by a chemical reaction. Preferable examples thereof include titanium compounds selected from titanium tetrachloride, titanium oxychloride, titanium sulfate, titanium nitrate, titanium alkoxide, hydrous titanium oxide (including those obtained by subjecting a titanium compound to hydrolysis in advance under alkaline conditions as well) and the like.

The concentration of the titanium compound in the aqueous solution to be used in the present invention is 0.07 to 5 mol/L and preferably from 0.1 to 1 mol/L, which is presented as a concentration of the Ti content of the titanium compound (hereafter simply referred to as "Ti concentration").

When the Ti concentration is lower than 0.07 mol/L, an anatase-type titanium oxide is formed. On the other hand, when the Ti content concentration is higher than 5 mol/L, the formation of titanium oxide is prevented because the water concentration is lowered.

The pH of the aforementioned aqueous solution containing the titanium compound is varies depending on the type of the chelating agent and the titanium compound to be used. For that reason, the pH of the aqueous solution containing the titanium compound is adjusted by using hydrochloric acid, nitric acid or the like, as needed.

The pH of the aqueous solution containing the titanium compound is adjusted in the range of −1 to 3. However, when the pH is greater than 3 for the reaction, it is not preferable because the formation of a titanium oxide crystal is prevented.

The aqueous solution containing the above chelating agent and the titanium compound after the pH is adjusted is usually maintained at a temperature selected from the temperature of −10 to 100 degree centigrade. The temperature in the range of 20 to 60 degree centigrade is preferably recommended. The temperature of the aqueous solution is usually maintained within the above temperature range for 0.5 to 10 hours.

As described above, ultrafine particles of a rutile-type titanium oxide are precipitated in the aqueous solution by maintaining the pH of the aqueous solution of a titanium compound having a Ti concentration of 0.07 to 5 mol/L in the range of −1 to 3 in the presence of a chelating agent. Incidentally, the aqueous solution contains a small amount of aggregate in which ultrafine particles of a rutile-type titanium oxide aggregate.

Ultrafine particles precipitated in the aqueous solution are those of a rutile-type titanium oxide. Such a fact can be confirmed by the X-ray diffraction measurement. Furthermore, an average particle diameter of the ultrafine particles of a rutile-type titanium oxide can be obtained from the Debye-Sherrer equation as well.

The ultrafine particle of a rutile-type titanium oxide precipitated in the above aqueous solution has an average particle diameter of 2 to 10 nm in short axis thereof and 15 to 30 nm in long axis thereof. The aggregate in which ultrafine particles of a rutile-type titanium oxide aggregate to one another has an average particle diameter of 10 to 100 nm.

Ultrafine particles of a rutile-type titanium oxide and an aggregate formed by aggregation of ultrafine particles of a rutile-type titanium oxide are separated by a method such as filtration or the like from the aqueous solution containing them, and as needed, are washed by a method such as dispersion into a solvent such as water and/or alcohol, ultrafiltration, reprecipitation or the like.

The thus recovered ultrafine particles of a rutile-type titanium oxide (including an aggregate formed by aggregation of ultrafine particles of a rutile-type titanium oxide) are dried or calcined at 100 to 800 degree centigrade, whereby the ultrafine particles may be obtained as the powder, but the ultrafine particles may also be obtained as a sol, as desired.

Since the thus obtained ultrafine particles of a rutile-type titanium oxide act as a catalyst in a photodecomposition reaction or the like, they are useful as a photocatalyst containing the ultrafine particles. Examples of the photodecomposition reaction include a reaction for decomposing an organic compound such as an organic dye, formalin or aromatic hydrocarbon, and the like.

EXAMPLES

The present invention is now more specifically illustrated below with reference to Examples. However, the present invention is not restricted to these Examples.

Incidentally, the activity of a photocatalyst is evaluated in accordance with the following method.

To a 1 cm cuvette cell, 6 mg of titanium oxide $TiO_2$ (in case of a sol, a sol containing $TiO_2$ in the same amount) was charged. To this cubette cell, $2 \times 10^{-5}$ mol/L of an aqueous methylene blue solution was added and the resulting mixture was stirred with a magnetic stirrer. The cuvette cell was irradiated at the side thereof with light from a high pressure xenon lamp through a water filter having a length of 5 cm. The amount of light in the front surface of the cell was measured and adjusted to 120 mW/cm$^2$. The sample solution was taken out at intervals of every 10 minutes and centrifuged to measure a UV-VIS absorption spectrum of the filtrate, and evaluate the photocatalytic activity from the change in absorbance of methylene blue.

Example 1

To a 100 mL eggplant flask, 0.001 mole ratio to 25 mmol of Ti that is 0.025 mmol of glycolic acid and 50 mL of ion exchange water were added. Subsequently, to the flask, 5 mL of a $TiOCl_2 \cdot HCl$ solution (Ti content: 25 mmol, a product of Fluka) was added to prepare a 0.45 M $TiOCl_2$ solution. This solution was allowed to react at 50 degree centigrade for 1 hour. The obtained precipitate was redispersed in ion exchange water for carrying out the electron microscope observation. As a result, a mixture containing ultrafine particles having an average particle diameter of 25 nm in long axis and 10 nm in short axis, and a small amount of aggregate of ultrafine particles having an average particle diameter of 50 nm was obtained. The obtained precipitate was washed with acetonitrile and air-dried to give powder. The X-ray diffraction spectrum of the air-dried powder was measured. As a result, the powder was identified as a rutile-type titanium oxide.

Figure 1:
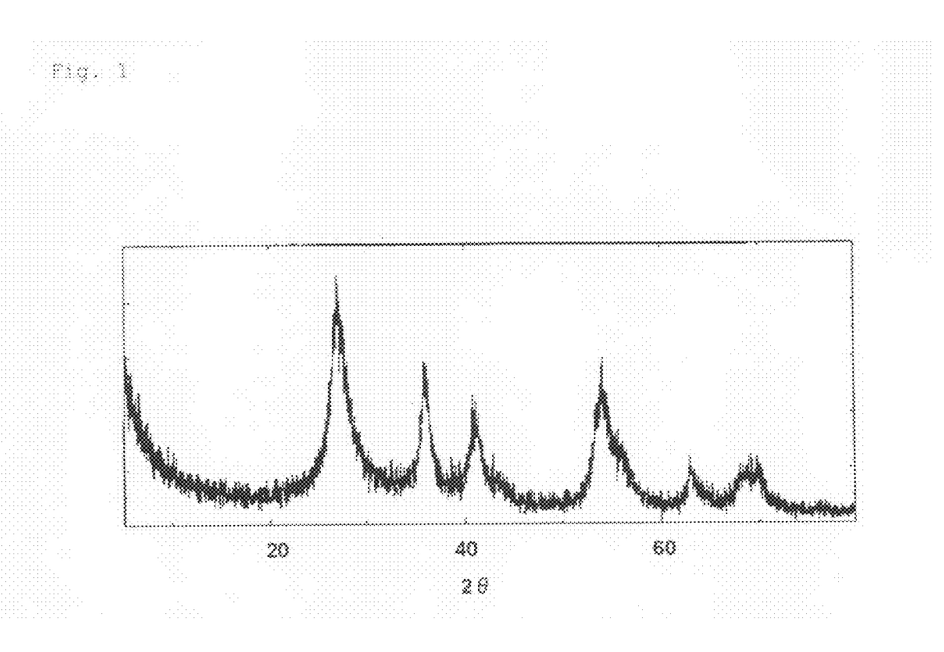
FIG. 1 is a diagram illustrating an X-ray diffraction spectrum of the air-dried powder obtained in Example 1.
Figure 2:
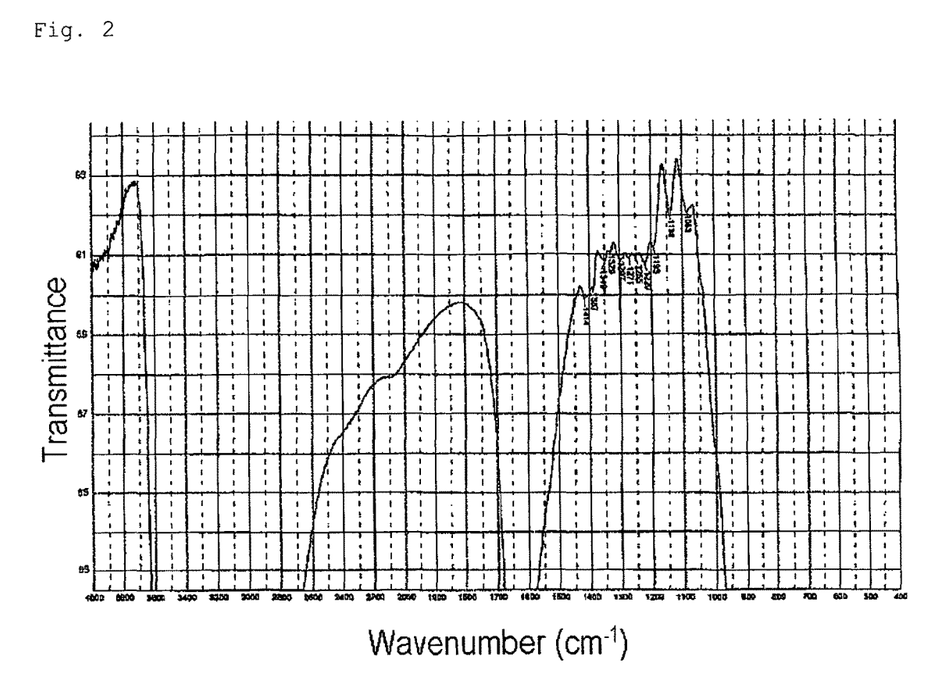
FIG. 2 is a diagram illustrating an infrared absorption spectrum of the air-dried powder obtained in Example 1.

The X-ray diffraction spectrum and infrared absorption spectrum of the air-dried powder are shown in FIGS. 1 and 2, respectively. Furthermore, the calculated values in the long axis and short axis of ultrafine particles evaluated from the Debye-Sherrer equation correspond to the results from the electron microscope observation.

The air-dried powder and the powder obtained by putting the air-dried powder in a crucible and calcining at 400 degree centigrade for 2 hours were each tested for the photocatalytic activity and as a result, it was found that they had high activity. The results were shown in FIG. 3.

Example 2

The same operations as in Example 1 were carried out except that lactic acid was used instead of glycolic acid. As a result, a mixture of ultrafine particles having an average particle diameter of 20 nm in long axis and 8 nm in short axis, and a small amount of aggregate of ultrafine particles having an average particle diameter of 30 nm was obtained.

Example 3

The same operations as in Example 1 were carried out except that acetylacetone was used instead of glycolic acid. As a result, a mixture containing ultrafine particles having an average particle diameter of 20 nm in long axis and 7 nm in short axis, and a small amount of aggregate of ultrafine particles having an average particle diameter of 25 nm was obtained.

Example 4

The same operations as in Example 1 were carried out except that succinic acid was used instead of glycolic acid. As a result, a mixture containing ultrafine particles having an average particle diameter of 25 nm in long axis and 12 nm in short axis, and a small amount of aggregate of ultrafine particles having an average particle diameter of 40 nm was obtained.

Example 5

Preparation of a Sample Plate a for the Test on Decomposition of Acetoaldehyde

To 100 mL polyethylene vessel, 5.0 g of the photocatalyst of ultrafine particles of a rutile-type titanium oxide obtained by calcining at 400 degree centigrade for 2 hours in Example 1 was charged, and 50.0 g of a glass bead having a diameter of 1 mm, 44.0 g of ethanol, 0.5 g of 1 N hydrochloric acid and 0.5 g of a nonionic surfactant (TritonX-100, registered trademark owned by Union Carbide) were additionally added and sealed. The sealed vessel was placed in a stainless ball mill pot having inner volume of 300 mL and fixed by filling the empty space of the pot with cloth such that the vessel was set in the middle of the ball mill pot. The ball mill pot was tightly sealed, and then it was set on the ball mill rotator and subjected to dispersion treatment at 60 rpm for 18 hours. After the treatment, the vessel was taken out, and the content was filtered through a nylon mesh sheet for removing the glass bead to obtain an ethanol dispersion of a photocatalyst of ultrafine particles of a rutile-type titanium oxide. Then, a slide glass (2.6 cm×7.6 cm, thickness: 1 mm) which was weighed in advance was immersed in and pulled up from the dispersion 42 times at intervals of every 90 seconds with a speed of 0.4 cm/s. Thus, the photocatalyst of ultrafine particles of a rutile-type titanium oxide was deposited on a surface of the slide glass. The photocatalyst deposited on the surface other than a surface of a 2.6 cm width was all wiped off. The resulting plate was calcined at 400 degree centigrade for 3 hours in an air atmosphere by using an electric furnace to prepare a photocatalyst-deposited sample plate A. The weights before and after deposition of the photocatalyst were measured and the thickness of the deposited layer of the photocatalyst of ultrafine particles of a rutile-type titanium oxide was measured, whereby it was found that, in the sample plate, the weight of the deposited photocatalyst of ultrafine particles of a rutile-type titanium oxide was 6.6 mg, the deposited area thereof was 12.2 cm$^2$, and the deposited quantity per area was 5.4 g/cm$^2$.

Test on Decomposition of Acetoaldehyde

The photocatalyst-deposited sample plate A was irradiated with ultraviolet light of 5.4 mW/cm$^2$ for 3 hours in an air atmosphere. A 27 W black-blue light (Sankyo, FPL27BLB) was used as a light source. UVA-365 (a product of Custom) was used for the measurement of UV intensity.

The photocatalyst-deposited sample plate A irradiated with UV light was attached to the center inside a 1 L Tedlar (registered trademark owned by DuPont) bag equipped with one each of a silicon packing-attached connector and a mini-cock using a double-sided adhesive tape of 5 mm square. At this time, one side of the bag was cut once, and after attaching the sample plate A, the cut part was tightly sealed by using a heat sealer. Subsequently, air inside the bag was pumped out through the mini-cock using a vacuum pump and the cock was closed, and the sample plate was allowed to stand in the dark overnight at a state that it was vacuum-packed.

Figure 4:
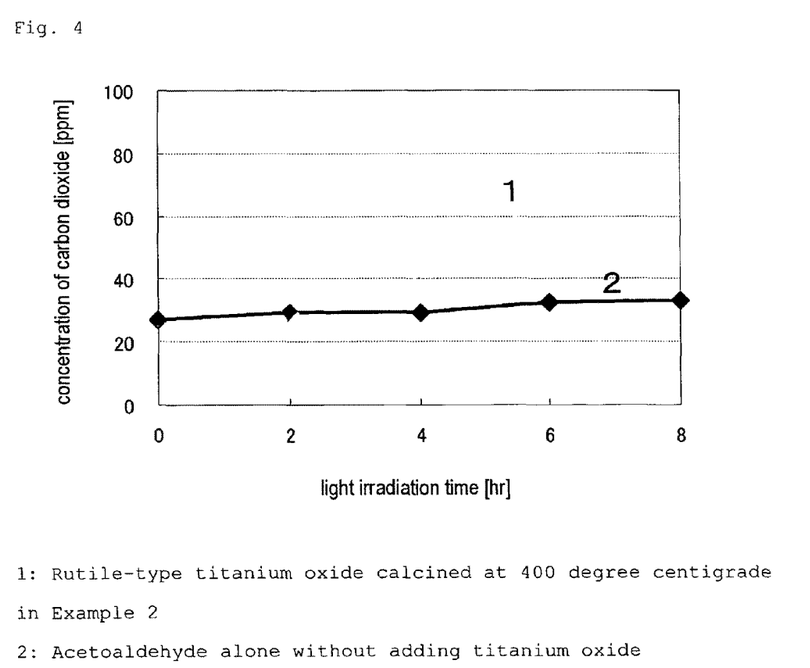
FIG. 4 is a diagram illustrating the results from the test on decomposition of acetaldehyde in Example 5.

Then, a wet mixed gas obtained by passing a mixed gas of 20% of oxygen and 80% of nitrogen through ion exchange water at 15 degree centigrade was mixed with a mixed gas of 1% acetoaldehyde and nitrogen to prepare a gas having an acetoaldehyde concentration of 96 ppm. 600 mL of the gas was collected and introduced into the bag with the photocatalyst-deposited sample plate A attached thereinside. Then, the bag was allowed to stand in the dark for 20 hours. Subsequently, the acetoaldehyde concentration and carbon dioxide concentration of the gas inside the bag were measured. A gas chromatograph (a product of Shimazu, GC-10A) equipped with a methanizer was used for the measurement of concentration. After the analysis, the bag with the photocatalyst-deposited sample plate A attached thereinside was placed such that the deposited surface of the photocatalyst-deposited sample plate A was at a distance of 4 cm from a white fluorescent lamp (a product of Matsushita Electric Works, Ltd., 10W, FL10N), and irradiated with the light perpendicularly. So, the gas inside the bag was analyzed at intervals of every 2 hours in the course of irradiation by a fluorescent lamp. At this time, the UV intensity measured at the same place as the deposited surface using a sheet of film as a filter that is the same as the bag was 11 μW/cm$^2$. Herein, UVA-365 (a product of Custom) was used for the measurement of UV intensity. The transition of carbon dioxide concentration was shown in FIG. 4. By irradiating with light from a fluorescent lamp, it was confirmed that acetoaldehyde was decomposed, and accordingly carbon dioxide was formed.

Example 6

Preparation of a Plate Sample B for the Test on Decomposition of Toluene

A photocatalyst-deposited sample plate B was prepared in the same manner as in Example 5 except that the treatment cycle of immersion and pulling-up was 40 times. In the sample plate, the weight of the deposited photocatalyst of ultrafine particles of a rutile-type titanium oxide was 5.8 mg, the deposited area thereof was 12.3 cm$^2$, and the deposited quantity per area was 4.7 g/cm$^2$.

Test on Decomposition of Toluene

Figure 5:
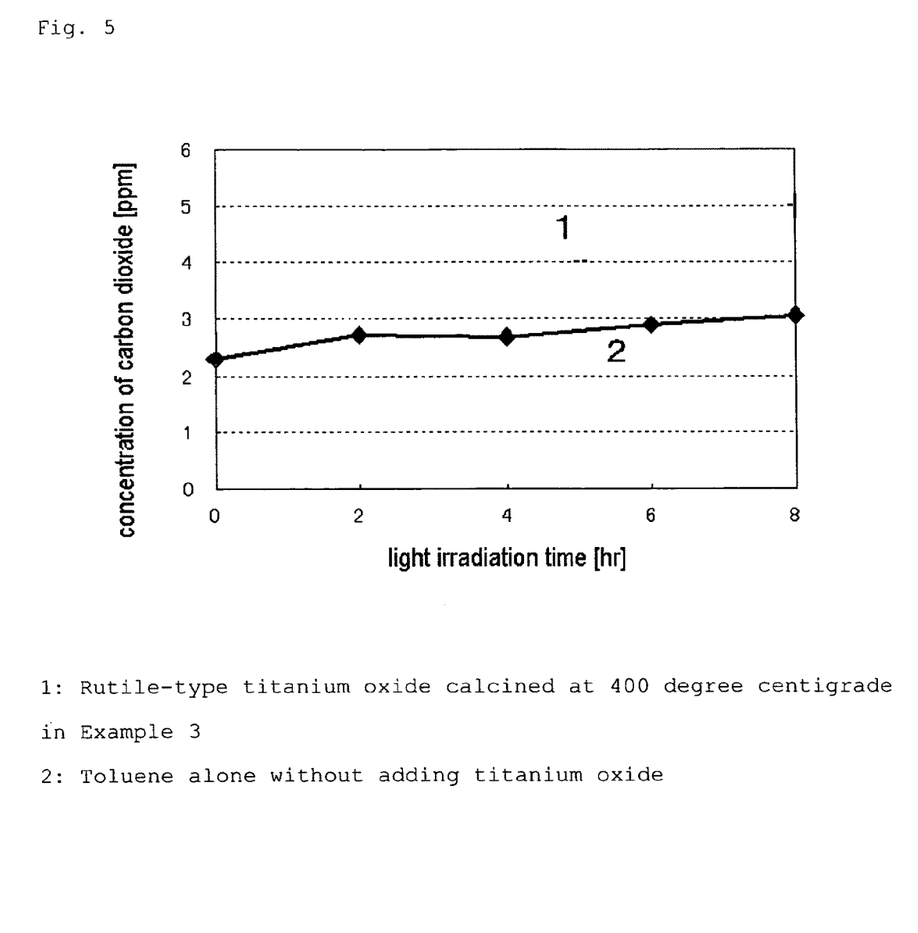
FIG. 5 is a diagram illustrating the results from the test on decomposition of toluene in Example 6.

The same operations as in Example 5 were carried out except that the photocatalyst-deposited sample plate B was used instead of the photocatalyst-deposited sample plate A, toluene was used instead of acetoaldehyde, and a mixed gas containing toluene having a toluene concentration of 31 ppm was used instead of a mixed gas containing acetoaldehyde having a acetoaldehyde concentration of 96 ppm. Decomposition reaction of toluene was carried out by irradiating light from a fluorescent lamp. The transition of carbon dioxide concentration was shown in FIG. 5. By irradiating with light of a fluorescent lamp, it was confirmed that toluene was decomposed, and accordingly carbon dioxide was formed.

Comparative Example 1

The same operations as in Example 1 were carried out except that glycolic acid was not added. As a result, an aggregate of ultrafine particles of a rutile-type titanium oxide could be prepared. The obtained ultrafine particles had difficulties in redispersing in an aqueous solution after being precipitated and filtered. An average particle diameter of ultrafine particles obtained from the Debye-Scherrer equation of X-ray diffraction was the same as that in Example 1, while an average particle diameter of the aggregate of ultrafine particles was large, that was 270 nm.

Comparative Example 2

An anatase-type titanium oxide was prepared in the following manner.

To 250 mL of ion exchange water, 2.5 mL of a $TiOCl_2.HCl$ solution (a product of Fluka) was added to give a 0.05 M $TiOCl_2$ solution. This solution was heated at 60 degree centigrade for 5 hours to give a sol. By adding acetonitrile to this sol, the precipitate was obtained and dried to obtain powder. From a result of X-ray diffraction, the obtained powder was found to be an anatase-type crystal. The spherical ultrafine particle had an average particle diameter of 5 nm according to the electron microscope observation and aggregation was hardly found.

Figure 3:
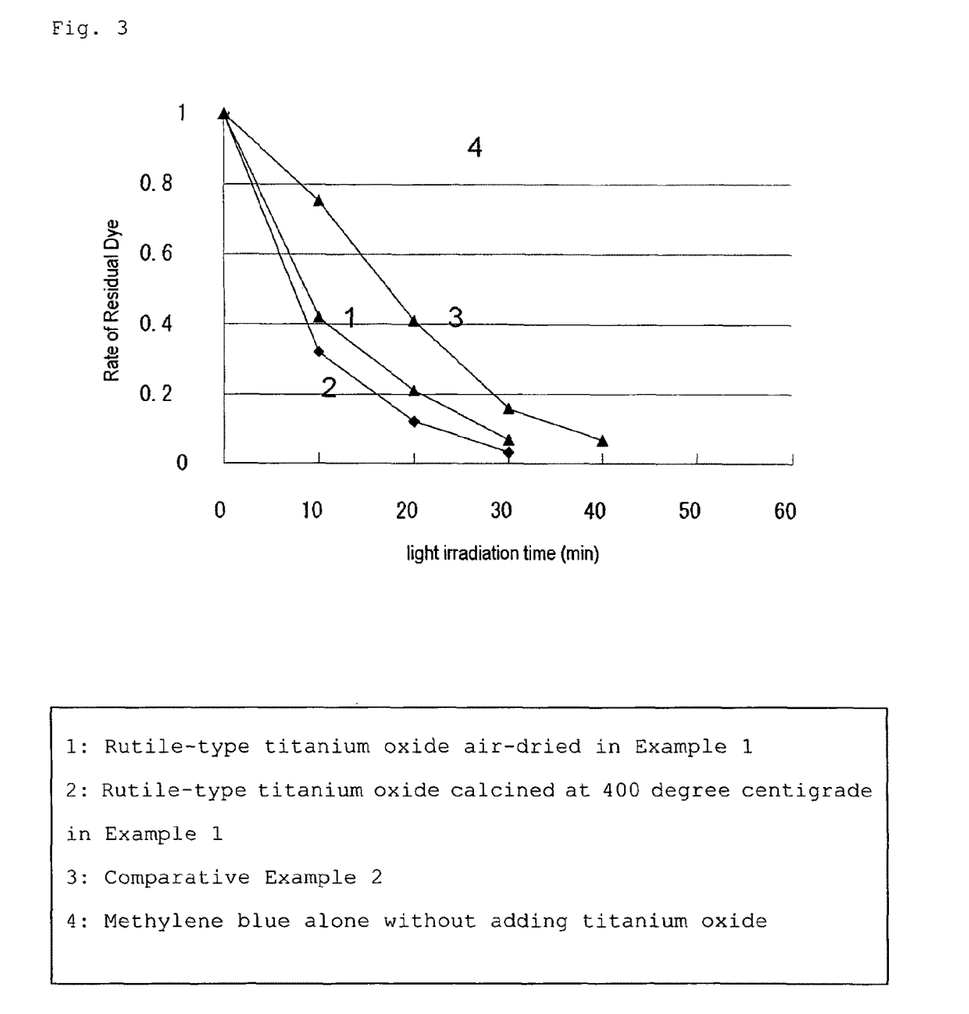
FIG. 3 is a diagram illustrating the results from the test on the photocatalytic activity of the air-dried powder of the rutile-type titanium oxide obtained in Example 1, the powder of the rutile-type titanium oxide subjected to calcination at 400 degree centigrade and the powder of the anatase-type titanium oxide obtained in Comparative Example 2.

The obtained powder was tested for its photocatalytic activity and the results thereof were shown in FIG. 3.

The invention claimed is:

1. A method for preparing ultrafine particles of a rutile-type titanium oxide, comprising maintaining the pH of an aqueous solution of a titanium compound having a Ti concentration of 0.07 to 5 mol/L in the range of −1 to 3 in the presence of a chelating agent, and precipitating the rutile-type titanium oxide in the aqueous solution,
wherein an average diameter of said ultrafine particles is from 2 nm to 12 nm in short axis and an average diameter of said ultrafine particles is from 15 nm to 25 nm in long axis, and
wherein the chelating agent is one or more selected from hydroxycarboxylic acids, diketones, and keto esters.

2. The method according to claim 1, wherein the hydroxycarboxylic acid is glycolic acid, lactic acid, citric acid, tartaric acid or salts thereof.

3. The method according to claim 1, wherein the diketone is acetylacetone or salts thereof.

4. The method according to claim 1, comprising adding the chelating agent in a mole ratio of the chelating agent to titanium of 0.0005 to 0.05.

5. A method for preparing an aggregate comprising ultrafine particles of a rutile-type titanium oxide, comprising maintaining the pH of an aqueous solution of a titanium compound having a Ti concentration of 0.07 to 5 mol/L in the range of −1 to 3 in the presence of a chelating agent, and precipitating the rutile-type titanium oxide in the aqueous solution,
wherein an average diameter of said aggregate is from 10 nm to 100 nm, and
wherein the chelating agent is one or more selected from hydroxycarboxylic acids, diketones, and keto esters.

6. The method for preparing an aggregate comprising ultrafine particles of a rutile-type titanium oxide according to claim 5, wherein the hydroxycarboxylic acid is glycolic acid, lactic acid, citric acid, tartaric acid or salts thereof.

7. The method according to claim 5, wherein the diketone is acetylacetone or salts thereof.

8. The method according to claim 5, comprising adding the chelating agent in a mole ratio of the chelating agent to titanium of 0.0005 to 0.05.

* * * * *